(12) United States Patent
Wang et al.

(10) Patent No.: US 12,141,972 B2
(45) Date of Patent: Nov. 12, 2024

(54) MEDICINE IMAGE RECOGNITION METHOD, ELECTRONIC DEVICE AND READABLE STORAGE MEDIUM

(71) Applicant: Fulian Precision Electronics (Tianjin) Co., LTD., Tianjin (CN)

(72) Inventors: Yu-Jen Wang, New Taipei (TW); Meng-Ping Lu, New Taipei (TW)

(73) Assignee: Fulian Precision Electronics (Tianjin) Co., LTD., Tianjin (CN)

(*) Notice: Subject to any disclaimer, the term of this patent is extended or adjusted under 35 U.S.C. 154(b) by 402 days.

(21) Appl. No.: 17/844,161

(22) Filed: Jun. 20, 2022

(65) Prior Publication Data

US 2023/0196558 A1 Jun. 22, 2023

(30) Foreign Application Priority Data

Dec. 16, 2021 (CN) .......................... 202111547632.6

(51) Int. Cl.
| | |
|---|---|
| *G06T 7/00* | (2017.01) |
| *G06N 3/084* | (2023.01) |
| *G06V 10/44* | (2022.01) |
| *G06V 10/74* | (2022.01) |
| *G06V 10/774* | (2022.01) |
| *G06V 10/82* | (2022.01) |
| *G06V 30/148* | (2022.01) |
| *G16H 20/10* | (2018.01) |
| *G16H 30/20* | (2018.01) |

(52) U.S. Cl.
CPC ........... *G06T 7/0012* (2013.01); *G06N 3/084* (2013.01); *G06V 10/44* (2022.01); *G06V 10/761* (2022.01); *G06V 10/774* (2022.01); *G06V 10/82* (2022.01); *G06V 30/153* (2022.01); *G16H 20/10* (2018.01); *G16H 30/20* (2018.01); *G06T 2207/20081* (2013.01); *G06T 2207/20084* (2013.01)

(58) Field of Classification Search
CPC ...... G06T 7/0012; G16H 30/20; G16H 20/10; G06V 10/761; G06V 30/153; G06V 10/82; G06V 10/44; G06V 10/774; G06N 3/084

See application file for complete search history.

(56) References Cited

U.S. PATENT DOCUMENTS 10,176,399 B1 * 1/2019 Rivard ................. G06V 30/153
11,495,338 B1 * 11/2022 Sternlicht ............. G16H 50/20
(Continued)

FOREIGN PATENT DOCUMENTS

| CN | 113301883 A | 8/2021 |
|---|---|---|
| TW | 202119354 A | 5/2021 |

*Primary Examiner* — David Bilodeau
(74) *Attorney, Agent, or Firm* — ScienBiziP, P.C.

(57) ABSTRACT

A medicine image recognition method applied to an electronic device is provided. The method includes obtaining target images by inputting medicine images into a position detection network. Character feature matrices are generated according to the target images and a character recognition network. Image feature matrices are generated by inputting the target images into a category recognition network. Reference matrices are generated according to the image feature matrices and corresponding character feature matrices. Once a matrix to be tested is generated by processing an image to be tested, and a recognition result of the image to be tested is generated according to a similarity between the matrix to be tested and each of the reference matrices.

20 Claims, 3 Drawing Sheets

(56) References Cited

U.S. PATENT DOCUMENTS

| | | | | |
|---|---|---|---|---|
| 2017/0053094 | A1* | 2/2017 | Hoenick | G16H 40/67 |
| 2021/0090699 | A1* | 3/2021 | Poirier | H04N 23/57 |
| 2021/0249139 | A1* | 8/2021 | Thakore | G06V 30/424 |
| 2022/0180447 | A1* | 6/2022 | Kearney | G06N 3/047 |
| 2022/0223262 | A1* | 7/2022 | Takashima | G16H 30/40 |

* cited by examiner

MEDICINE IMAGE RECOGNITION METHOD, ELECTRONIC DEVICE AND READABLE STORAGE MEDIUM

FIELD

The present disclosure relates to image processing technology, in particular to a medicine image recognition method, an electronic device, and a readable storage medium.

BACKGROUND

In a method for recognizing images of medications, a lot of manpower is required to apply labels to medication appearing in medicine images which are used as training data for training a recognition model. If an amount of the training data is too small, an accuracy of recognition of the training model is low. Therefore, there is a room to improve the accuracy of recognizing medicine images.

DETAILED DESCRIPTION

In order to provide a more clear understanding of the objects, features, and advantages of the present disclosure, the same are given with reference to the drawings and specific embodiments. It should be noted that the embodiments in the present disclosure and the features in the embodiments may be combined with each other without conflict.

In the following description, numerous specific details are set forth in order to provide a full understanding of the present disclosure. The present disclosure may be practiced otherwise than as described herein. The following specific embodiments are not to limit the scope of the present disclosure.

Unless defined otherwise, all technical and scientific terms herein have the same meaning as used in the field of the art technology as generally understood. The terms used in the present disclosure are for the purposes of describing particular embodiments and are not intended to limit the present disclosure.

Figure 1:
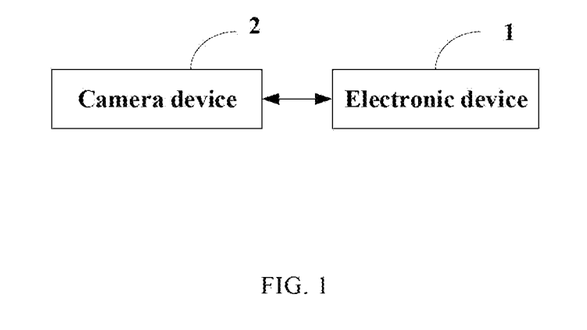
FIG. 1 is an environment diagram of an embodiment of a medicine image recognition method.

FIG. 1 is a flowchart of one embodiment of a medicine image recognition method of the present disclosure. According to different requirements, a sequence of each block in this flowchart can be adjusted according to actual requirements, and some blocks can be omitted. The execution body of this method can be an electronic device, such as an electronic device 1 shown in FIG. 3.

The medicine image recognition method can be applied to one or more electronic devices 1. The electronic device 1 can communicate with a camera device 2, and the camera device 2 may be a camera or other device for capturing images. For example, the camera device 2 can take an image of a medicine to be tested to obtain an image of the medicine to be tested. The medicine to be tested can be capsules or tablets, for example, amoxicillin capsules, clarithromycin dispersible tablets, and the like.

The electronic device 1 is a device that can automatically perform numerical calculation and/or information processing according to pre-set or stored instructions, and its hardware includes, but is not limited to, a microprocessor, an application specific integrated circuit (ASIC), a field-programmable gate array (FPGA), a digital signal processor (DSP), an embedded equipment, and so on.

The electronic device 1 can be any electronic product that can interact with a user. For example, the electronic device 1 can be a personal computer, a tablet computer, a smart phone, a personal digital assistant (PDA), a game console, and an internet protocol television (IPTV), a smart wearable device, etc.

The electronic device 1 may also include network equipment and/or user equipment. Wherein, the network device includes, but is not limited to, a network server, a server group formed by a plurality of network servers, or a cloud formed by a large number of hosts or network servers based on cloud computing.

The network where the electronic device 1 is located includes, but is not limited to, the Internet, a wide area network, a metropolitan area network, a local area network, a virtual private network (VPN), and the like.

Figure 2:
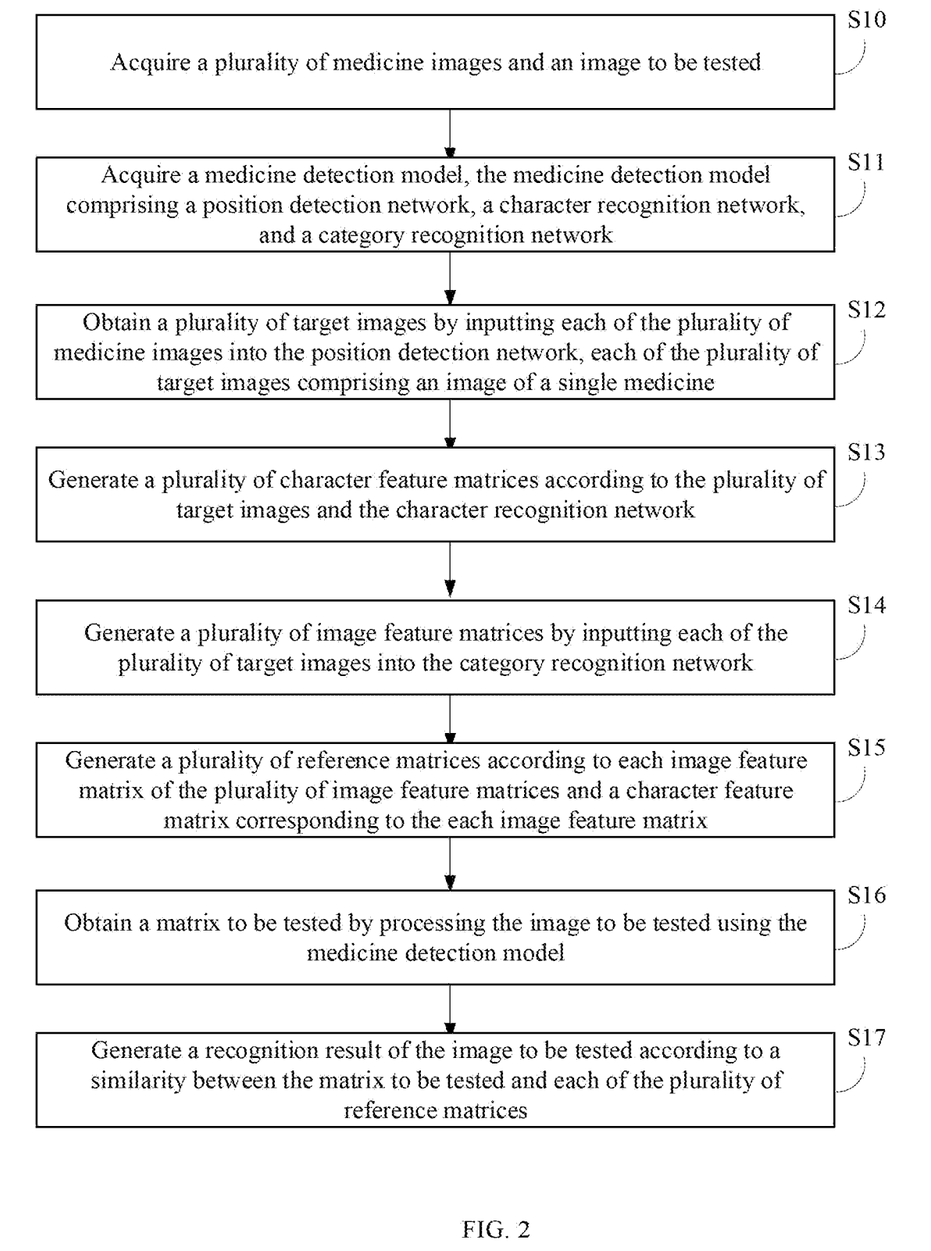
FIG. 2 is a flowchart of an embodiment of a method for recognizing medicines in an image.

At block S10, the electronic device acquires a plurality of medicine images and an image to be tested.

In at least one embodiment, each of the plurality of medicine images refers to an image taken of at least one medicine. Each of the plurality of medicine images includes label information, and the plurality of medicine images can be used to generate reference matrices.

The label information may include, but is not limited to, a name of each medicine contained in the image, a category of the each medicine, a usage of the each medicine, and the like.

In at least one embodiment, the electronic device acquires the plurality of medicine images and the label information corresponding to each medicine image from a preset target database.

In at least one embodiment, the electronic device obtains the image to be tested by controlling the camera device 2 to capture image of at least one medicine that is to be tested.

In at least one embodiment, the image to be tested does not includes the label information. In at least one embodiment, there are characters on a surface of the at least one medicine to be tested, and the characters describe information of the at least one medicine to be tested, the characters may be letters, and/or numbers.

At block S11, the electronic device acquires a medicine detection model, where the medicine detection model includes a position detection network, a character recognition network, and a category recognition network.

In at least one embodiment, the medicine detection model may be a network model for detecting a location of each medicine in the image to be tested and detecting a location of each medicine in each medicine image.

In at least one embodiment, the position detection network can be used to frame an image of each single medicine from each medicine image. For example, the image of each single medicine can be enframed from the medicine image using a rectangular frame.

In at least one embodiment, the character recognition network can be used to recognize character information in each medicine image.

In at least one embodiment, the category recognition network can be used to identify a category of each medicine in each medicine image.

At block S12, the electronic device obtains a plurality of target images by inputting each of the plurality of medicine images into the position detection network, each of the plurality of target images includes an image of a single medicine.

In at least one embodiment, each target image refers to an image containing an appearance of a single medicine which is enframed from each medicine image.

In at least one embodiment, the electronic device obtains the position detection network by:

Acquiring a position detection learner and position images, the position images include first images and second images, the second images include a plurality of labeled images and a plurality of unlabeled images; obtaining a first pre-training network by training the position detection learner using the first images; obtaining a first labeling network by adjusting the first pre-training network based on the plurality of labeled images; obtaining a plurality of output images and a predicted probability value of each medicine contained in each of the plurality of output images by inputting the plurality of unlabeled images into the first labeling network; obtaining a second labeling network by adjusting the first labeling network based on each output image corresponding to the predicted probability value being greater than a preset threshold; calculating a first loss value of the second labeling network: adjusting the second labeling network based on the first loss value until the first loss value decreases to a minimum value, such that the position detection network is obtained, i.e., determining the second labeling network to be the position detection network when the first loss value decreases to the minimum value.

Specifically, the "adjusting the second labeling network based on the first loss value until the first loss value decreases to a minimum value, such that the position detection network is obtained" includes:

Inputting each output image corresponding to the predicted probability value greater than the preset threshold into the first labeling network for training, and iteratively updating a weight of the first labeling network until the first labeling network reaches convergence to obtain the position detection network.

Wherein, the position detection learner can be a target detector such as efficientDet. The position detection learner can be used to accurately locate a position of each single medicine in each medicine image. The electronic device may acquire the first images from a first database in advance. The first images each of which may be an image containing any object. The first database may be a COCO database, an ImageNet database, a CPTN database, or other databases. Each of the first images may include a plurality of categories of objects such as animals (e.g., puppy, kitten, etc.), plants (e.g., flowers, trees, etc.). The second images each of which refers to an image containing an appearance of at least one medicine, and the electronic device may acquire the second images from a second database in advance. Each of the plurality of labeled images refers to an image in which a position of the at least one medicine in the images has been labeled, and each of the plurality of unlabeled images refers to an image in which a position of the at least one medicine in the images is not labeled.

Each of the plurality of output images refers to an image that may include a single medicine, and each output image can be used to make a plurality of adjustments to the first labeling network.

The predicted probability value refers to a probability that an appearance of a single medicine is contained in the output image.

The preset threshold can be set according to requirements, which is not limited in this disclosure.

The electronic device obtains the first pre-training network by using the first images for training.

The electronic device obtains the first labeling network after retraining the first pre-training network according to the plurality of labeled images, and the first labeling network can be used to label features on each of the plurality of unlabeled images.

A formula for calculating the first loss value is:

$$FL(p_t) = -\alpha_t(1-p_t)^\gamma \log(p_t):$$

Wherein, $FL(p_t)$ represents the first loss value, $p_t$ represents the predicted probability value, and $\alpha_t \in [0,1]$, $\gamma \geq 0$.

Through the above implementations, the electronic device can select the second labeling network with a smallest first loss value as the position detection network. Because the second labeling network has learned the features of the plurality of labeled images, the position detection network can accurately label each medicine image.

At block S13, the electronic device generates a plurality of character feature matrices according to the plurality of target images and the character recognition network.

In at least one embodiment, each of the plurality of character feature matrices refers to a matrix that includes character features in one of the plurality of target images, and each character feature matrix can be used to generate a reference matrix.

In at least one embodiment, the electronic device acquires the character recognition network by:

Acquiring character images and a character recognition learner, the character images include third images and fourth images; obtaining a second pre-training network by training the character recognition learner using the third images, wherein the second pre-training network includes a convolutional neural network model and a recurrent neural network model; calculating a second loss value of the second pre-training network, and adjusting parameters of the second pre-training network based on the second loss value by back-propagation until the second pre-training network reaches convergence, such that the character recognition network is obtained, i.e., determining the second pre-training network to be the character recognition network when the second pre-training network reaches convergence.

Wherein, the character recognition learner refers to a learner that recognizes the characters in each medicine image, the character images refer to images used to train the character recognition learner, and each character image contains characters on a medicine.

The convolutional neural network model may be a VGG16 network, and the convolutional neural network model may be used to extract character features of the fourth images. The recurrent neural network model may be a long short-term memory (LSTM) network, and the recurrent neural network model may be used to extract information of time series of the character features.

The third images may be used to train weights of the character recognition learner. The fourth images refer to images each of which containing characters on one medicine. The characters on a medicine can include, but are not limited to, letters and numbers. The electronic device may obtain the third images from the first database. The electronic device may acquire the fourth images from a third database, where a plurality of images of medicine with characters are stored in the third database.

A loss function of the second pre-training network may be a connectionist temporal classification loss (CTC) function.

Through the above embodiments, the electronic device selects the second pre-training network corresponding to a lowest second loss value as the character recognition network, which can improve the reliability and accuracy of the character recognition network, so that the character recognition network can accurately extract the character features of each target image.

In at least one embodiment, the generating of the plurality of character feature matrices according to the plurality of target images and the character recognition network includes:

Obtaining a plurality of grayscale images by performing color conversion on each of the plurality of target images; obtaining a plurality of binarized images by performing binarization on each of the plurality of grayscale images; obtaining a plurality of filtered images by filtering each of the plurality of binarized images; locating a position of characters in each of the plurality of filtered images; obtaining a plurality of framed images by enframing an image of characters in each target image of the plurality of target images according to the position of characters in the each target image; obtaining a plurality of feature sequences by inputting each of the plurality of enframed images into the convolutional neural network model for extracting features; and obtaining the plurality of character feature matrices by inputting each of the plurality of feature sequences into the recurrent neural network model.

Wherein, each feature sequence refers to features extracted from each filtered image by the convolutional neural network model, and each of the plurality of character feature matrices refers to features obtained by the recurrent neural network model extracted from each feature sequence.

Through the above-mentioned embodiments, the electronic device performs color conversion, binarization, filtering and other processing on each target image, so as to obtain a clearer filtered image, and the features can be accurately obtained according to the plurality of filtered images, facilitating the generating of the character feature matrix.

At block S14, the electronic device generates a plurality of image feature matrices by inputting each of the plurality of target images into the category recognition network.

In at least one embodiment, each of the plurality of image feature matrices refers to a matrix including image features in one of the plurality of target images.

In at least one embodiment, the electronic device acquires the category recognition network by:

Acquiring a category recognition learner, in which a soft-max function is used as an activation function; calculating a third loss value of the category recognition learner; adjusting the category recognition learner based on the third loss value until the third loss value decreases to a minimum value; and obtaining the category recognition network by deleting the activation function from the adjusted category recognition learner.

Specifically, the "acquiring a category recognition learner, in which a soft-max function is used as an activation function" includes:

Constructing the category recognition learner based on a resnet50 network; and determining the soft-max function as the activation function.

In at least one embodiment, the calculating of the third loss value of the category recognition learner includes:

Acquiring a plurality of category images, the plurality of category images corresponding to a plurality of categories; obtaining a plurality of augmented images by augmenting the plurality of category images, wherein the plurality of augmented images are in pairs, each pair of augmented images includes a first augmented image and a second augmented image, and the first augmented image and the second augmented image are obtained by augmenting a same category image.

Each of the plurality of category images refers to an output image corresponding to the predicted probability value that is greater than the preset threshold.

The data augmentation processing refers to performing transformations such as rotation and cropping on each category image.

The plurality of categories include, but are not limited to, antibiotics, vitamins, and the like.

A formula for calculating the third loss value is:

$$L_{in}^{sup} = \sum_{i=1}^{2N} \frac{-1}{2N_{yi}-1} \sum_{j=1}^{2N} \|_{i \neq j} \cdot \|_{yi=yj} \cdot \log \frac{\exp(z_i \cdot z_j / \tau)}{\sum_{k=1}^{2N} \|_{i \neq k} \cdot \exp(z_i \cdot z_k / \tau)};$$

Wherein, $L_{in}^{sup}$ represents the third loss value, 2N represents the plurality of augmented images, i represents the i th augmented image in the plurality augmented images, yi represents the category of the i th augmented image, j represents the jth augmented image in the augmented images of the same category as i, yj represents the category of the jth augmented image, $N_{yi}$ represents a number of all augmented images with the same category as i; $\|_{i \neq j}$ represents a first indicator function which takes zero if and only if i=j, and takes 1 when i≠j; $\|_{yi=yj}$ represents a second indicator function which takes zero if and only if yi=yj, and takes 1 when yi≠yj; $\|_{i \neq k}$ represents a third indicator function which takes zero if and only if i=k, and takes 1 when i≠k; $z_i$ represents a unit vector obtained by input i into in the category recognition network, $z_j$ represents to the unit vector obtained by inputting j into the category identification network, k represents any one augmented image except i, and $z_k$ represents a unit vector obtained by inputting k into the category recognition network, and τ represents a preset parameter of scalar adjustment.

Through the above embodiment, the electronic device performs data augmentation processing on the plurality of category images, augments the training data, such that more training data is used to train the category recognition network, which can improve an accuracy of identification of the category recognition network.

At block S15, the electronic device generates a plurality of reference matrices according to each image feature matrix of the plurality of image feature matrices and a character feature matrix corresponding to the each image feature matrix.

In at least one embodiment, a character feature matrix corresponding to an image feature matrix indicates that a target image used for generating the character feature matrix and a target image used for generating the image feature matrix are same image.

In at least one embodiment, each reference matrix refers to a matrix including image features and character features of one of the plurality of target images, and the reference matrix can be used to indicate label information of the image to be tested.

In at least one embodiment, the generating of the plurality of reference matrices according to each image feature matrix of the plurality of image feature matrices and the character feature matrix corresponding to the each image feature matrix includes:

Generating each reference matrix by adding each image feature matrix and the corresponding character feature matrix, wherein each image feature matrix and the corresponding character feature matrix have a same number of rows and a same number of columns.

In at least one embodiment, the electronic device may generate the each reference matrix in other ways, for example, the electronic device generates the each reference matrix by multiplying each image feature matrix and the corresponding character feature matrix. Alternatively, the electronic device generates the reference matrix by performing a subtraction operation on each image feature matrix and the corresponding character feature matrix.

Through the above embodiments, the electronic device can extract the image features and character features of the medicine in each medicine image, and generate a reference matrix that includes both the image features and the character features.

At block S16, the electronic device obtains a matrix to be tested by processing the image to be tested using the medicine detection model.

In at least one embodiment, the matrix to be tested refers to a matrix including image features and character features of the image to be tested.

Since a process of generating the matrix to be tested is the same as a process of generating the reference matrix, details are not described herein.

Through the above-mentioned embodiment, the electronic device obtains the matrix to be tested by processing the image to be tested using a same method of processing the plurality of medicine images, so that the matrix to be tested and each reference matrix have the same number of rows and the number of columns, it is more convenient to calculate a similarity between the matrix to be tested and each reference matrix.

At block S17, the electronic device generates a recognition result of the image to be tested according to a similarity between the matrix to be tested and each of the plurality of reference matrices.

In at least one embodiment, the recognition result refers to label information corresponding to the medicine to be tested.

In at least one embodiment, the generating of the recognition result of the image to be tested according to the similarity between the matrix to be tested and each of the plurality of reference matrices includes:

Calculating the similarity between the matrix to be tested and each of the plurality of reference matrices; determining the reference matrix corresponding to a maximum similarity as the target matrix; obtaining the recognition result by performing mapping process on the target matrix based on a preset label mapping table.

The preset label mapping table refers to a mapping table between each reference matrix and corresponding label information, and each reference matrix in the preset label mapping table has a one-to-one correspondence with the label information.

The similarity may be a cosine similarity or a Euclidean distance.

A formula of calculating the cosine similarity is:

$$\cosine = \frac{\sum_{i=1}^{n} A_i \times B_i}{\sqrt{\sum_{i=1}^{n} (A_i)^2} \times \sqrt{\sum_{i=1}^{n} (B_i)^2}};$$

Wherein cosine represents the cosine similarity, n represents all elements in the matrix to be tested and any one reference matrix of the plurality of reference matrices, i represents the ith element in the matrix to be tested and the any one reference matrix, and $A_i$ represents the ith element in the matrix to be tested, i represents the ith element in the any one reference matrix.

Specifically, the obtaining of the recognition result by performing mapping process on the target matrix based on the preset label mapping table includes:

Determining the label information corresponding to the medicine to be tested in the preset label mapping table according to the target matrix; and determining the corresponding label information as the recognition result.

Through the above-mentioned embodiment, the electronic device selects the reference matrix corresponding to the maximum similarity as the target matrix, so that the medicine image corresponding to the target matrix is more similar to the image to be tested, and the corresponding medicine image is the label information which is used as the label information of the medicine to be tested. According to the one-to-one correspondence between the target matrix and the label information, the label information of the medicine to be tested can be quickly found, which improves the efficiency of recognizing the medicine image.

It can be seen from the above technical solutions that the position detection network is obtained by performing a plurality of adjustments to the second pre-training network using the plurality or labeled images, because the position detection network has learned the features of the plurality of labeled images, so the position detection network can label the position of the image to be tested, and when training the category recognition network, the data augmentation processing is performed on the plurality of category images, thus avoiding a sparsity of the training data. The electronic device generates a plurality of reference matrices according to each image feature matrix and the corresponding character feature matrix, generates the matrix to be tested abased on the image to be tested using a same method, and calculates the similarity between the matrix to be tested and each reference matrix, and selects the label information of the reference matrix corresponding to the maximum similarity as the recognition result, because the matrix to be tested contains the character features and image features of the image to be tested at the same time, so that the matrix to be tested can comprehensively to reflect the characteristics of the image to be tested, so that the accuracy of the recognition result is higher.

Figure 3:
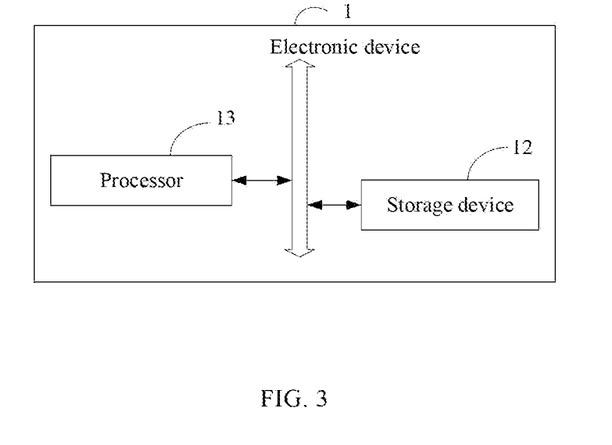
FIG. 3 is a structural diagram of an embodiment of an electronic device.

As shown in FIG. 3, it is a structural diagram of an electronic device according to one embodiment of the medicine image recognition method of the present disclosure.

In an embodiment of the present disclosure, the electronic device 1 includes, but is not limited to, a storage device 12, a processor 13, and a computer program stored in the storage device 12 and can be executed by the processor 13. For example, the computer program can be a program of medicine image recognition.

Those skilled in the art can understand that the schematic structural diagram is only an example of the electronic device 1, and does not constitute a limitation on the electronic device 1, and may include more or less components than the one shown, or combine some components, or different components, for example, the electronic device 1 may also include input and output devices, network access devices, buses, and the like.

The processor 13 may be a central processing unit (CPU), or other general-purpose processors, a digital signal processor (DSP), an application specific integrated circuit (ASIC), Field-Programmable Gate Array (FPGA) or other programmable logic devices, discrete gate or transistor logic devices, discrete hardware components, etc. The general-purpose processor can be a microprocessor or the processor can also be any conventional processor, etc. The processor 13 is the computing core and control center of the electronic device 1, and uses various interfaces and lines to connect each part of the electronic device 1.

The processor 13 obtains the operating system of the electronic device 1 and obtains various installed applications. The processor 13 obtains the application program to implement each block in the embodiments of the foregoing medicine image recognition method, for example, to implement each block shown in FIG. 1.

Exemplarily, the computer program can be divided into one or more modules/units, and the one or more modules/units are stored in the storage device 12 and retrieved by the processor 13 to complete the present disclosure. The one or more modules/units may be a series of computer program instruction segments capable of performing specific functions, and the instruction segments are used to describe the process of acquisition the computer program in the electronic device 1.

The storage device 12 can be used to store the computer programs and/or modules, and the processor 13 executes or obtains the computer programs and/or modules stored in the storage device 12, and calls up the data stored in the storage device 12, such that various functions of the electronic device 1 are realized. The storage device 12 may mainly include an area for storing programs and an area for storing data, wherein the area for storing programs may store an operating system, an application program required for at least one function (such as a sound playback function, an image playback function, etc.), and the like; the area for storing data may store the data created according to the use of the electronic device 1. In addition, the storage device 12 may include non-volatile storage device such as hard disk, internal memory, plug-in hard disk, smart media card (SMC), Secure digital (SD) card, flash card, at least one disk storage device, flash memory device, or other non-volatile solid state storage device.

The storage device 12 may be an external storage device and/or an internal storage device of the electronic device 1. Further, the storage device 12 may be a storage in physical form, such as a memory stick, a trans-flash card, and the like.

If the modules/units integrated in the electronic device 1 are implemented in the form of software functional units and sold or used as independent products, they may be stored in a computer-readable storage medium. Based on this understanding, the present disclosure can implement all or part of the processes in the methods of the above embodiments, and can also be completed by instructing the relevant hardware through a computer program. The computer program can be stored in a computer-readable storage medium, and when the computer program is acquired by the processor, the blocks of the foregoing method embodiments can be implemented.

Wherein, the computer program includes computer program code, and the computer program code may be in the form of source code, object code, obtainable file or some intermediate form, and the like. The computer-readable medium may include: any entity or device capable of carrying the computer program code, recording medium, U disk, removable hard disk, magnetic disk, optical disk, computer memory, read-only memory (ROM).

With reference to FIG. 2, the storage device 12 in the electronic device 1 stores a plurality of instructions to implement the medicine image recognition method, and the processor 13 can acquire the plurality of instructions to implement processes of: acquiring a plurality of medicine images and an image to be tested; acquiring a medicine detection model, the medicine detection model comprising a position detection network, a character recognition network, and a category recognition network; obtaining a plurality of target images by inputting each of the plurality of medicine images into the position detection network, each of the plurality of target images comprising an image of a single medicine; generating a plurality of character feature matrices according to the plurality of target images and the character recognition network; generating a plurality of image feature matrices by inputting each of the plurality of target images into the category recognition network; generating a plurality of reference matrices according to each image feature matrix of the plurality of image feature matrices and a character feature matrix corresponding to the each image feature matrix; obtaining a matrix to be tested by processing the image to be tested using the medicine detection model; and generating a recognition result of the image to be tested according to a similarity between the matrix to be tested and each of the plurality of reference matrices.

Specifically, for the specific implementation method of the above-mentioned instruction by the processor 13, reference may be made to the description of the relevant blocks in the corresponding embodiment of FIG. 1, and details are not repeated.

In the several embodiments provided in this disclosure, it should be understood that the devices and methods disclosed can be implemented by other means. For example, the device embodiments described above are only schematic. For example, the division of the modules is only a logical function division, which can be implemented in another way.

The modules described as separate parts may or may not be physically separate, and the parts displayed as modules may or may not be physical units, that is, may be located in one place, or may be distributed over multiple network units. Part or all of the modules can be selected according to the actual needs to achieve the purpose of this embodiment.

In addition, each functional unit in each embodiment of the present disclosure can be integrated into one processing unit, or can be physically present separately in each unit, or two or more units can be integrated into one unit. The above integrated unit can be implemented in a form of hardware or in a form of a software functional unit.

The above integrated modules implemented in the form of function modules may be stored in a storage medium. The above function modules may be stored in a storage medium, and include several instructions to enable a computing device (which may be a personal computer, server, or network device, etc.) or processor to execute the method described in the embodiment of the present disclosure.

The present disclosure is not limited to the details of the above-described exemplary embodiments, and the present disclosure can be embodied in other specific forms without departing from the spirit or essential characteristics of the present disclosure. Therefore, the present embodiments are to be considered as illustrative and not restrictive, and the scope of the present disclosure is defined by the appended claims. All changes and variations in the meaning and scope of equivalent elements are included in the present disclosure. Any reference sign in the claims should not be construed as limiting the claim. Furthermore, the word "comprising" does not exclude other units nor does the singular exclude the plural. A plurality of units or devices stated in the system claims may also be implemented by one unit or device through software or hardware. Words such as "first" and "second" are used to indicate names but not to signify any particular order.

The above description is only embodiments of the present disclosure and is not intended to limit the present disclosure, and various modifications and changes can be made to the present disclosure. Any modifications, equivalent substitutions, improvements, etc. made within the spirit and scope of the present disclosure are intended to be included within the scope of the present disclosure.

What is claimed is:

1. A medicine image recognition method applied to an electronic device, the method comprising:
   acquiring a plurality of medicine images and an image to be tested;
   acquiring a medicine detection model, the medicine detection model comprising a position detection network, a character recognition network, and a category recognition network;
   obtaining a plurality of target images by inputting each of the plurality of medicine images into the position detection network, each of the plurality of target images comprising an image of a single medicine;
   generating a plurality of character feature matrices according to the plurality of target images and the character recognition network;
   generating a plurality of image feature matrices by inputting each of the plurality of target images into the category recognition network;
   generating a plurality of reference matrices according to each image feature matrix of the plurality of image feature matrices and a character feature matrix corresponding to the each image feature matrix;
   obtaining a matrix to be tested by processing the image to be tested using the medicine detection model; and
   generating a recognition result of the image to be tested according to a similarity between the matrix to be tested and each of the plurality of reference matrices.

2. The medicine image recognition method according to claim 1, further comprising:
   obtaining the position detection network by:
   acquiring a position detection learner and position images, the position images comprising first images and second images, the second images comprising a plurality of labeled images and a plurality of unlabeled images;
   obtaining a first pre-training network by training the position detection learner using the first images;
   obtaining a first labeling network by adjusting the first pre-training network based on the plurality of labeled images;
   obtaining a plurality of output images and a predicted probability value of each medicine contained in each of the plurality of output images by inputting the plurality of unlabeled images into the first labeling network;
   obtaining a second labeling network by adjusting the first labeling network based on each output image corresponding to the predicted probability value greater than a preset threshold;
   calculating a first loss value of the second labeling network; and
   adjusting the second labeling network based on the first loss value till the first loss value decreases to a minimum value, and determining the second labeling network to be the position detection network in response that the first loss value decreases to the minimum value.

3. The medicine image recognition method according to claim 1, further comprising:
   acquiring the character recognition network by:
   acquiring character images and a character recognition learner, the character images comprising third images and fourth images;
   obtaining a second pre-training network by training the character recognition learner using the third images, the second pre-training network comprising a convolutional neural network model and a recurrent neural network model;
   calculating a second loss value of the second pre-training network;
   adjusting parameters of the second pre-training network based on the second loss value by back propagating until the second pre-training network reaches convergence, and determining the second pre-training network to be the character recognition network in response that the second pre-training network reaches convergence.

4. The medicine image recognition method according to claim 3, wherein the generating of the plurality of character feature matrices according to the plurality of target images and the character recognition network comprises:
   obtaining a plurality of grayscale images by performing color conversion on each of the plurality of target images;
   obtaining a plurality of binarized images by performing binarization processing on each of the plurality of grayscale images;
   obtaining a plurality of filtered images by filtering each of the plurality of binarized images;
   locating a position of characters in each of the plurality of filtered images;
   obtaining a plurality of framed images by framing an image of characters in each target image of the plurality of target images according to the position of characters in the each target image;
   obtaining a plurality of feature sequences by inputting each of the plurality of framed images into the convolutional neural network model for extracting features; and
   obtaining the plurality of character feature matrices by inputting each of the plurality of feature sequences into the recurrent neural network model.

5. The medicine image recognition method according to claim 1, further comprising:
   acquiring the category recognition network by:
   acquiring a category recognition learner, in which a soft-max function is used as an activation function;
   calculating a third loss value of the category recognition learner;
   adjusting the category recognition learner based on the third loss value until the third loss value decreases to a minimum value; and
   obtaining the category recognition network by deleting the activation function from the adjusted category recognition learner.

6. The medicine image recognition method according to claim 5, wherein the calculating of the third loss value of the category recognition learner comprises:
   acquiring a plurality of category images, the plurality of category images corresponding to a plurality of categories;
   obtaining a plurality of augmented images by augmenting the plurality of category images;
   wherein a formula of calculating the third loss value is:

$$L_{in}^{sup} = \sum_{i=1}^{2N} \frac{-1}{2N_{yi}-1} \sum_{j=1}^{2N} \|_{i \neq j} \cdot \|_{yi=yj} \cdot \log \frac{\exp(z_i \cdot z_j / \tau)}{\sum_{k=1}^{2N} \|_{i \neq k} \cdot \exp(z_i \cdot z_k / \tau)};$$

wherein, $L_{in}^{sup}$ represents the third loss value, 2N represents to the plurality of augmented images, i represents to the i th augmented image in the plurality augmented images, yi represents to the category of the i th augmented image, j represents to the jth augmented image in the augmented images of the same category as i, yj represents to the category of the jth augmented image, $N_{yi}$ represents to a number of all augmented images with the same category as i; $\|_{i \neq j}$ represents a first indicator function which takes zero if and only if i=j, and takes 1 when i≠j; $\|_{yi=yj}$ represents a second indicator function which takes zero if and only if yi=yj, and takes 1 when yi≠yj; $\|_{i \neq k}$ represents a third indicator function which takes zero if and only if i=k, and takes 1 when i≠k; $z_i$ represents a unit vector obtained by input i into in the category recognition network, $z_i$ represents to the unit vector obtained by inputting j into the category identification network, k represents to any one augmented image except i, and $z_k$ represents a unit vector obtained by inputting k into the category recognition network, and τ represents a preset parameter of scalar adjustment.

7. The medicine image recognition method according to claim 1, wherein the generating of the plurality of reference matrices according to each image feature matrix of the plurality of image feature matrices and the character feature matrix corresponding to the each image feature matrix comprises:
generating each reference matrix by adding each image feature matrix and the corresponding character feature matrix, wherein each image feature matrix and the corresponding character feature matrix have a same number of rows and a same number of columns.

8. The medicine image recognition method according to claim 1, wherein the generating of the recognition result of the image to be tested according to the similarity between the matrix to be tested and each of the plurality of reference matrices comprises:
calculating the similarity between the matrix to be tested and each of the plurality of reference matrices;
determining the reference matrix corresponding to a maximum similarity as the target matrix; and
obtaining the recognition result by performing mapping processing on the target matrix based on a preset label mapping table.

9. An electronic device comprising:
a storage device;
at least one processor; and
the storage device storing one or more programs, which when executed by the at least one processor, cause the at least one processor to:
acquire a plurality of medicine images and an image to be tested;
acquire a medicine detection model, the medicine detection model comprising a position detection network, a character recognition network, and a category recognition network;
obtain a plurality of target images by inputting each of the plurality of medicine images into the position detection network, each of the plurality of target images comprising an image of a single medicine;
generate a plurality of character feature matrices according to the plurality of target images and the character recognition network;
generate a plurality of image feature matrices by inputting each of the plurality of target images into the category recognition network;
generate a plurality of reference matrices according to each image feature matrix of the plurality of image feature matrices and a character feature matrix corresponding to the each image feature matrix;
obtain a matrix to be tested by processing the image to be tested using the medicine detection model; and
generate a recognition result of the image to be tested according to a similarity between the matrix to be tested and each of the plurality of reference matrices.

10. The electronic device according to claim 9, wherein the at least one processor is further caused to:
obtain the position detection network by:
acquiring a position detection learner and position images, the position images comprising first images and second images, the second images comprising a plurality of labeled images and a plurality of unlabeled images;
obtaining a first pre-training network by training the position detection learner using the first images;
obtaining a first labeling network by adjusting the first pre-training network based on the plurality of labeled images;
obtaining a plurality of output images and a predicted probability value of each medicine contained in each of the plurality of output images by inputting the plurality of unlabeled images into the first labeling network;
obtaining a second labeling network by adjusting the first labeling network based on each output image corresponding to the predicted probability value greater than a preset threshold;
calculating a first loss value of the second labeling network; and
adjusting the second labeling network based on the first loss value till the first loss value decreases to a minimum value, and determining the second labeling network to be the position detection network in response that the first loss value decreases to the minimum value.

11. The electronic device according to claim 9, wherein the at least one processor is further caused to:
acquire the character recognition network by:
acquiring character images and a character recognition learner, the character images comprising third images and fourth images;
obtaining a second pre-training network by training the character recognition learner using the third images, the second pre-training network comprising a convolutional neural network model and a recurrent neural network model;
calculating a second loss value of the second pre-training network;
adjusting parameters of the second pre-training network based on the second loss value by back propagating until the second pre-training network reaches convergence, and determining the second pre-training network to be the character recognition network in response that the second pre-training network reaches convergence.

12. The electronic device according to claim 11, wherein the at least one processor generates the plurality of character feature matrices according to the plurality of target images and the character recognition network by:

obtaining a plurality of grayscale images by performing color conversion on each of the plurality of target images;
obtaining a plurality of binarized images by performing binarization processing on each of the plurality of grayscale images;
obtaining a plurality of filtered images by filtering each of the plurality of binarized images;
locating a position of characters in each of the plurality of filtered images;
obtaining a plurality of framed images by framing an image of characters in each target image of the plurality of target images according to the position of characters in the each target image; obtaining a plurality of feature sequences by inputting each of the plurality of framed images into the convolutional neural network model for extracting features; and
obtaining the plurality of character feature matrices by inputting each of the plurality of feature sequences into the recurrent neural network model.

13. The electronic device according to claim 9, wherein the at least one processor is further caused to:
acquire the category recognition network by:
acquiring a category recognition learner, in which a soft-max function is used as an activation function;
calculating a third loss value of the category recognition learner;
adjusting the category recognition learner based on the third loss value until the third loss value decreases to a minimum value; and
obtaining the category recognition network by deleting the activation function from the adjusted category recognition learner.

14. The electronic device according to claim 13, wherein the at least one processor calculates the third loss value of the category recognition learner by:
acquiring a plurality of category images, the plurality of category images corresponding to a plurality of categories;
obtaining a plurality of augmented images by augmenting the plurality of category images;
wherein a formula of calculating the third loss value is:

$$L_{in}^{sup} = \sum_{i=1}^{2N} \frac{-1}{2N_{yi}-1} \sum_{j=1}^{2N} \|_{i \neq j} \cdot \|_{yi=y} \cdot \log \frac{\exp(z_i \cdot z_j / \tau)}{\sum_{k=1}^{2N} \|_{i \neq k} \cdot \exp(z_i \cdot z_k / \tau)};$$

wherein, $L_{in}^{sup}$ represents the third loss value, 2N represents to the plurality of augmented images, i represents to the i th augmented image in the plurality augmented images, yi represents to the category of the i th augmented image, j represents to the jth augmented image in the augmented images of the same category as i, yj represents to the category of the jth augmented image, $N_{yi}$ represents to a number of all augmented images with the same category as i; $\|_{i \neq j}$ represents a first indicator function which takes zero if and only if i=j, and takes 1 when i≠j; $\|_{yi=yj}$ represents a second indicator function which takes zero if and only if yi=yj, and takes 1 when yi≠yj; $\|_{i \neq k}$ represents a third indicator function which takes zero if and only if i=k, and takes 1 when i≠k; $z_i$ represents a unit vector obtained by input i into the category recognition network, $z_j$ represents to the unit vector obtained by inputting j into the category identification network, k represents to any one augmented image except i, and $z_k$ represents a unit vector obtained by inputting k into the category recognition network, and τ represents a preset parameter of scalar adjustment.

15. The electronic device according to claim 9, wherein the at least one processor generates the plurality of reference matrices according to each image feature matrix of the plurality of image feature matrices and the character feature matrix corresponding to the each image feature matrix by:
generating each reference matrix by adding each image feature matrix and the corresponding character feature matrix, wherein each image feature matrix and the corresponding character feature matrix have a same number of rows and a same number of columns.

16. The electronic device according to claim 9, wherein the at least one processor generates the recognition result of the image to be tested according to the similarity between the matrix to be tested and each of the plurality of reference matrices by:
calculating the similarity between the matrix to be tested and each of the plurality of reference matrices;
determining the reference matrix corresponding to a maximum similarity as the target matrix; and
obtaining the recognition result by performing mapping processing on the target matrix based on a preset label mapping table.

17. A non-transitory storage medium having instructions stored thereon, when the instructions are executed by a processor of an electronic device, the processor is caused to perform a medicine image recognition method, wherein the method comprises:
acquiring a plurality of medicine images and an image to be tested;
acquiring a medicine detection model, the medicine detection model comprising a position detection network, a character recognition network, and a category recognition network;
obtaining a plurality of target images by inputting each of the plurality of medicine images into the position detection network, each of the plurality of target images comprising an image of a single medicine;
generating a plurality of character feature matrices according to the plurality of target images and the character recognition network;
generating a plurality of image feature matrices by inputting each of the plurality of target images into the category recognition network;
generating a plurality of reference matrices according to each image feature matrix of the plurality of image feature matrices and a character feature matrix corresponding to the each image feature matrix;
obtaining a matrix to be tested by processing the image to be tested using the medicine detection model; and
generating a recognition result of the image to be tested according to a similarity between the matrix to be tested and each of the plurality of reference matrices.

18. The non-transitory storage medium according to claim 17, wherein the method further comprises:
obtaining the position detection network by:
acquiring a position detection learner and position images, the position images comprising first images and second images, the second images comprising a plurality of labeled images and a plurality of unlabeled images;
obtaining a first pre-training network by training the position detection learner using the first images;

obtaining a first labeling network by adjusting the first pre-training network based on the plurality of labeled images;

obtaining a plurality of output images and a predicted probability value of each medicine contained in each of the plurality of output images by inputting the plurality of unlabeled images into the first labeling network;

obtaining a second labeling network by adjusting the first labeling network based on each output image corresponding to the predicted probability value greater than a preset threshold;

calculating a first loss value of the second labeling network; and adjusting the second labeling network based on the first loss value till the first loss value decreases to a minimum value, and determining the second labeling network to be the position detection network in response that the first loss value decreases to the minimum value.

19. The non-transitory storage medium according to claim 17, wherein the method further comprises:

acquiring the character recognition network by:

acquiring character images and a character recognition learner, the character images comprise third images and fourth images;

obtaining a second pre-training network by training the character recognition learner using the third images, the second pre-training network comprising a convolutional neural network model and a recurrent neural network model;

calculating a second loss value of the second pre-training network;

adjusting parameters of the second pre-training network based on the second loss value by back propagating until the second pre-training network reaches convergence, and determining the second pre-training network to be the character recognition network in response that the second pre-training network reaches convergence.

20. The non-transitory storage medium according to claim 19, wherein the generating of the plurality of character feature matrices according to the plurality of target images and the character recognition network comprises:

obtaining a plurality of grayscale images by performing color conversion on each of the plurality of target images;

obtaining a plurality of binarized images by performing binarization processing on each of the plurality of grayscale images;

obtaining a plurality of filtered images by filtering each of the plurality of binarized images;

locating a position of characters in each of the plurality of filtered images;

obtaining a plurality of framed images by framing an image of characters in each target image of the plurality of target images according to the position of characters in the each target image; obtaining a plurality of feature sequences by inputting each of the plurality of framed images into the convolutional neural network model for extracting features; and obtaining the plurality of character feature matrices by inputting each of the plurality of feature sequences into the recurrent neural network model.

* * * * *